United States Patent
Elomari et al.

(10) Patent No.: US 10,099,936 B2
(45) Date of Patent: Oct. 16, 2018

(54) SYNTHESIS OF ZEOLITE SSZ-16

(71) Applicant: Chevron U.S.A. Inc., San Ramon, CA (US)

(72) Inventors: Saleh Ali Elomari, Fairfield, CA (US); Tracy Margaret Davis, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/839,099

(22) Filed: Dec. 12, 2017

(65) Prior Publication Data

US 2018/0111838 A1 Apr. 26, 2018

Related U.S. Application Data

(62) Division of application No. 15/433,031, filed on Feb. 15, 2017, now Pat. No. 9,868,643.

(60) Provisional application No. 62/339,279, filed on May 20, 2016.

(51) Int. Cl.
| | |
|---|---|
| *C07D 211/06* | (2006.01) |
| *C01B 39/48* | (2006.01) |
| *C01B 39/02* | (2006.01) |
| *B01J 29/70* | (2006.01) |
| *B01J 37/00* | (2006.01) |
| *B01J 37/04* | (2006.01) |
| *C07D 207/06* | (2006.01) |
| *C07D 211/26* | (2006.01) |

(52) U.S. Cl.
CPC ............... *C01B 39/48* (2013.01); *B01J 29/70* (2013.01); *B01J 37/0018* (2013.01); *B01J 37/04* (2013.01); *C01B 39/026* (2013.01); *C07D 207/06* (2013.01); *C07D 211/26* (2013.01); *C01P 2002/72* (2013.01); *C01P 2004/03* (2013.01)

(58) Field of Classification Search
CPC .................................................. C07D 211/06
See application file for complete search history.

(56) References Cited

FOREIGN PATENT DOCUMENTS

JP 33001369 A * 2/1958

OTHER PUBLICATIONS

Wislicenus, J. "Adolph Strecker's Short Textbook of Organic Chemistry" 1881, Spottiswoode: London, pp. 38-39.*
G. Sunagawa and T. Kushina "Synthesis of Cyclohexane Quaternary Ammonium Salts. The Reduction of Terephthalate." Yakugaku Zasshi, 1956, 76, 954-955.

* cited by examiner

*Primary Examiner* — David K O'Dell
(74) *Attorney, Agent, or Firm* — Terrence M. Flaherty (57) ABSTRACT

A method is disclosed for synthesizing a zeolite having the framework structure of SSZ-16 using a structure directing agent comprising a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium].

1 Claim, 3 Drawing Sheets

SYNTHESIS OF ZEOLITE SSZ-16

CROSS-REFERENCE TO RELATED APPLICATIONS

This application is a divisional of U.S. application Ser. No. 15/433,031, filed Feb. 15, 2017, which claims the benefit of U.S. Provisional Application Ser. No. 62/339,279, filed May 20, 2016, the contents of which are hereby incorporated by reference.

TECHNICAL FIELD

This disclosure relates to the synthesis of zeolite SSZ-16.

BACKGROUND

Molecular sieve materials, both natural and synthetic, have been demonstrated in the past to be useful as adsorbents and to have catalytic properties for various types of organic conversion reactions. Certain molecular sieves, such as zeolites, aluminophosphates, and mesoporous materials, are ordered, porous crystalline materials having a definite crystalline structure as determined by X-ray diffraction. Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Molecular sieves identified by the International Zeolite Association as having the framework type AFX are known. For example, the zeolite known as SSZ-16 is a known crystalline AFX framework type material.

U.S. Pat. No. 4,508,837 discloses zeolite SSZ-16 and its synthesis in the presence of a structure directing agent derived from 1,4-di(1-azoniabicyclo[2.2.2]octane) lower alkane compounds.

U.S. Pat. No. 5,194,235 discloses the synthesis of zeolite SSZ-16 in the presence of DABCO-$C_n$-diquat cations, where DABCO represents 1,4-diazabicyclo[2.2.2]octane and n is 3, 4 or 5.

R. H. Archer et al. (*Micropor. Mesopor. Mater.* 2010, 130, 255-265) disclose the synthesis of an aluminosilicate AFX framework type zeolite using 1,3-bis(1-adamantyl)imidazolium cations as a structure directing agent.

The commercial development of SSZ-16 has been hindered by the high cost of these structure directing agents and hence there has been significant interest in finding alternative, less expensive structure directing agents for the synthesis of SSZ-16.

According to the present disclosure, it has now been found that the organic dications described herein are effective as structure directing agents in the synthesis of SSZ-16.

SUMMARY

In one aspect, there is provided a method of synthesizing a zeolite having the framework structure of SSZ-16, the method comprising: (a) preparing a reaction mixture comprising: (1) a source of silicon oxide; (2) a source of aluminum oxide; (3) a source of a Group 1 or 2 metal; (4) a structure directing agent comprising a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium]; (5) hydroxide ions; and (6) water; and (b) subjecting the reaction mixture to crystallization conditions sufficient to form crystals of the zeolite.

In another aspect, there is provided a zeolite having the framework structure of SSZ-16 and comprising in its pores a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium].

In yet another aspect, there is provided an organic nitrogen-containing compound comprising a dication selected from one of the following structures:

DETAILED DESCRIPTION

Introduction

The term "as-synthesized" is employed herein to refer to a zeolite in its form after crystallization, prior to removal of the structure directing agent.

The term "anhydrous" is employed herein to refer to a zeolite substantially devoid of both physically adsorbed and chemically adsorbed water.

As used herein, the numbering scheme for the Periodic Table Groups is as disclosed in *Chem. Eng. News* 1985, 63(5), 26-27.

Reaction Mixture

In general, the present zeolite is synthesized by: (a) preparing a reaction mixture comprising (1) a source of silicon oxide; (2) a source of aluminum oxide; (3) a source of a Group 1 or 2 metal (M); (4) a structure directing agent (Q) comprising a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium]; (5) hydroxide ions; and (6) water; and (b) subjecting the reaction mixture to crystallization conditions sufficient to form crystals of the zeolite.

The composition of the reaction mixture from which the zeolite is formed, in terms of molar ratios, is identified in Table 1 below:

TABLE 1

| Reactants | Useful | Exemplary |
|---|---|---|
| $SiO_2/Al_2O_3$ | 5 to 100 | 10 to 50 |
| $M/SiO_2$ | 0.10 to 1.00 | 0.10 to 0.70 |
| $Q/SiO_2$ | 0.05 to 0.50 | 0.10 to 0.30 |
| $OH/SiO_2$ | 0.10 to 1.00 | 0.20 to 0.70 |
| $H_2O/SiO_2$ | 15 to 60 | 20 to 40 | wherein compositional variables M and Q are as described herein above.

Suitable sources of silicon oxide include fumed silica, colloidal silica, precipitated silica, alkali metal silicates, and tetraalkyl orthosilicates.

Suitable sources of aluminum oxide include hydrated alumina and water-soluble aluminum salts (e.g., aluminum nitrate).

Combined sources of silicon oxide and aluminum oxide can additionally or alternatively be used and include colloidal aluminosilicates, aluminosilicate zeolites (e.g., zeolite Y) and clays or treated clays (e.g., metakaolin).

Examples of suitable Group 1 or Group 2 metals (M) include sodium, potassium and calcium, with sodium being preferred. The metal (M) is preferably present in the reaction mixture as the hydroxide.

The structure directing agent (Q) comprises a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium]. The dications are represented by structures (1), (2), (3), and (4) below:

(1)

1,1'-(1,4-cyclohexylenedimethylene)bis[1-methylpiperidinium]

(2)

1,1'-(1,4-cyclohexylenedimethylene)bis[1-ethylpiperidinium]

(3)

1,1'-(1,4-cyclohexylenedimethylene)bis[1-methylpyrrolidinium]

(4)

1,1'-(1,4-cyclohexylenedimethylene)bis[1-ethylpyrrolidinium]

Suitable sources of Q are the hydroxides, chlorides, bromides, and/or salts of the relevant diquaternary ammonium compounds.

The reaction mixture may also contain seeds of a molecular sieve material, such as SSZ-16 from a previous synthesis, desirably in an amount of from 0.01 to 10,000 ppm by weight (e.g., from 100 to 5000 ppm by weight) of the reaction mixture.

The reaction mixture can be prepared either batch wise or continuously. Crystal size, morphology and crystallization time of the zeolite described herein can vary with the nature of the reaction mixture and the crystallization conditions.

Crystallization and Post-Synthesis Treatment

Crystallization of the present zeolite from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. (e.g., from 130° C. to 175° C.) for a time sufficient for crystallization to occur at the temperature used, e.g., from 1 day to 28 days. Crystallization is usually carried out in a closed system under autogenous pressure.

Once the zeolite crystals have formed, the solid product is recovered from the reaction mixture by standard mechanical separation techniques such as centrifugation or filtration. The recovered crystals are water-washed and then dried to obtain the as-synthesized zeolite crystals. The drying step is typically performed at a temperature of less than 200° C.

As a result of the crystallization process, the recovered crystalline zeolite product contains within its pore structure at least a portion of the structure directing agent used in the synthesis.

The as-synthesized zeolite may be subjected to treatment to remove part or all of the organic structure directing agent used in its synthesis. This is conveniently effected by thermal treatment in which the as-synthesized material is heated at a temperature of at least about 370° C. for at least 1 minute and generally not longer than 20 hours. The thermal treatment can be performed at a temperature up to 925° C. While sub-atmospheric pressure can be employed for the thermal treatment, atmospheric pressure is desired for reasons of convenience. Additionally or alternatively, the organic structure directing agent can be removed by treatment with ozone (see, e.g., A. N. Parikh et al., *Micropor. Mesopor. Mater.* 2004, 76, 17-22).

To the extent desired, the original Group 1 or 2 metal cations in the zeolite can be replaced in accordance with techniques well known in the art by ion exchange with other cations. Preferred replacing cations include metal ions (e.g., rare earth metals and metals of Groups 2 to 15 of the Periodic Table), hydrogen ions, hydrogen precursor ions (e.g., ammonium ions), and combinations thereof.

The present zeolite can be formulated with into a catalyst composition by combination with other materials, such as binders and/or matrix materials, which provide additional hardness or catalytic activity to the finished catalyst. When blended with such components, the relative proportions of SSZ-16 and matrix may vary widely with the SSZ-16 content ranging from 1 to 90 wt. % (e.g., from 2 to 80 wt. %) of the composite.

Characterization of the Zeolite

In its as-synthesized and anhydrous form, the present zeolite has a chemical composition, in terms of molar ratios, as described in Table 2 below:

TABLE 2

|  | Useful | Exemplary |
|---|---|---|
| $SiO_2/Al_2O_3$ | 5 to 50 | 5 to 25 |
| $Q/SiO_2$ | >0 to 0.2 | >0 to 0.1 |
| $M/SiO_2$ | >0 to 0.2 | >0 to 0.1 | wherein Q comprises a dication selected from one or more of 1,1'-(1,4-cyclohexylenedimethylene)bis[1-methylpiperidinium]; 1,1'-(1,4-cyclohexylenedimethylene)bis[1-ethylpiperidinium]; 1,1'-(1,4-cyclohexylenedimethylene)bis[1-methylpyrrolidinium]; and 1,1'-(1,4-cyclohexylenedimethylene)bis[1-ethylpyrrolidinium]; and M is a Group 1 or 2 metal.

It should be noted that the as-synthesized form of the present zeolite may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

As taught by U.S. Pat. No. 4,508,837, zeolite SSZ-16 has a powder X-ray diffraction pattern which includes at least the characteristic peaks set forth in Table 3 below.

TABLE 3

| 2-Theta | d-spacing (nm) | Relative Intensity[a] |
|---|---|---|
| 7.52 | 1.176 | M |
| 8.72 | 1.014 | VS |
| 11.59 | 0.763 | S |
| 15.71 | 0.564 | VS |
| 17.48 | 0.507 | VS |
| 17.66 | 0.502 | S |
| 20.46 | 0.434 | VS |
| 21.85 | 0.407 | VS |
| 27.68 | 0.322 | VS |
| 30.68 | 0.291 | VS |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

EXAMPLES

The following illustrative examples are intended to be non-limiting.

Example 1

Synthesis of 1,1'-(1,4-cyclohexylenedimethylene)bis [1-methylpiperidinium hydroxide]

A 2-liter three-neck reaction flask equipped with an overhead stirrer, a reflux condenser, and a heating mantle was charged with dichloromethane (800 mL), cyclohexane-1,4-dicarboxylic acid (100 g, 0.58 moles) and thionyl chloride (185 g). A trap containing water was connected to the reaction vessel through the top of the condenser to trap the produced HCl and $SO_2$ gases. The solution was heated at reflux for 4 hours and then left to stir at room temperature overnight or until bubble formation in the water trap ceased. The reaction mixture was then concentrated on a rotary evaporator at reduced pressure in hot water bath to give cyclohexane-1,4-dicarbonyl dichloride (120 g, 98% yield) as a slightly orange oil.

A three-neck 2-liter reaction flask equipped with an overhead stirrer, a reflux condenser, and an addition funnel was charged with cyclohexane (600 mL), triethylamine (75 g, 0.74 moles), and piperidine (48 g, 0.56 moles). The mixture was cooled to 0° C. (water-ice bath) and a solution of cyclohexane-1,4-dicarbonyl dichloride (60 g, 0.29 moles) in cyclohexane (50 mL) was added dropwise via the addition funnel. Once all the dichloride was added, the ice bath was replaced with a heating mantle and the reaction mixture was heated at reflux overnight. The resulting off-white solution (solids and solution) was cooled down to room temperature and water was added dropwise until all the solids dissolved. The resulting biphasic solution was transferred to a separatory funnel and the two phases were separated. The organic phase was diluted with ethyl acetate (250 mL) and washed with water (3×250 mL) and brine (300 mL). The aqueous layer was extracted with dichloromethane (2×150 mL). The dichloromethane extracts were added to the organic extracts and the combined organic extracts were dried over anhydrous magnesium sulfate, filtered and concentrated on a rotary evaporator to give the desired diamide, 1,1'-(1,4-cyclohexanediyldicarbonyl)dipiperidine, as light tan-colored solid in 94% (83.5 g) yield. The product was confirmed by NMR and IR spectroscopy.

A three-neck 2-liter reaction flask equipped with an overhead stirrer, a reflux condenser was charged with anhy- drous tetrahydrofuran (450 mL) and lithium aluminum hydride (29 g, 0.77 moles). The suspension was cooled down to 0° C. by means of an ice bath. Then, a solution of 1,1'-(1,4-cyclohexanediyldicarbonyl) dipiperidine (58 g) in tetrahydrofuran (100 mL) was added dropwise via a dropping funnel while stirring. Once all the diamide was added, the reaction mixture was allowed to gradually warm up to room temperature and then heated at reflux overnight. The reaction was worked up by cooling it down to 0° C. by means of a water-ice bath and diluting the mixture with tetrahydrofuran (200 mL). Then, an aqueous NaOH solution (15 wt. %, 200 mL) was added dropwise with vigorous stirring while keeping the reaction mixture temperature between 0° C. and 10° C. Once the addition of the NaOH solution was complete, water (20 mL) was added and the mixture was left to stir until the gray solution became a clear liquid and a white precipitate. The reaction mixture was filtered through a fritted glass funnel. The filtrate was dried over anhydrous magnesium sulfate, filtered and concentrated on a rotary evaporator at 15 torr and 75° C. to give 1,1'-(1,4-cyclohexylenedimethylene) dipiperidine (48.9 g, 94% yield) as yellow oil. The product was confirmed by NMR and IR spectroscopy.

In a 250 mL round bottom reaction flask, 1,1'-(1,4-cyclohexylenedimethylene)dipiperidine (30 g, 0.104 moles) was dissolved in methanol (250 mL). To this solution, iodomethane (46.6 g, 0.32 moles) was added and the mixture was allowed to stir for 48 hours. Additional iodomethane (8 g) was added and the reaction mixture was heated at reflux for several hours. NMR analysis showed the reaction was complete. The reaction mixture was concentrated on a rotary evaporator at reduced pressure and 70° C. to remove the solvent and the excess iodomethane. The obtained product, a dark tan solid, was purified by boiling in isopropyl alcohol (100 mL) to give brownish liquid and light tan solids. The mixture was left to cool down to room temperature and then diethyl ether (200 mL) was added to crystallize any dissolved product. The mixture was filtered and the solids were dried on a rotary evaporator at 26 torr and 75° C. The reaction afforded 1,1'-(1,4-cyclohexylenedimethylene)bis[1-methylpiperidinium iodide] (53.6 g, 89.3% yield) as an off-white solid.

The resulting diiodide salt was exchanged to the corresponding dihydroxide derivative by stirring it with OH-ion exchange resin (BIO-RAD® AH1-X8) in deionized water overnight. The solution was filtered and the filtrate was analyzed for hydroxide concentration by titration on a small sample. The exchange afforded 1,1'-(1,4-cyclohexylenedimethylene)bis[1-methylpiperidinium hydroxide] as a 0.65 molar solution (97% yield).

Example 2

Synthesis of 1,1'-(1,4-cyclohexylenedimethylene)bis [1-ethylpiperidinium hydroxide]

In a 250 mL round bottom reaction flask, 1,1'-(1,4-cyclohexylenedimethylene)dipiperidine (25 g, 0.09 moles), synthesized as described in Example 1, was dissolved in methanol (150 mL). To this solution, iodoethane (56 g, 0.36 moles) was added and the mixture was allowed to stir for 72 hours. Then, additional iodoethane (10 g) was added and the reaction was heated at reflux for 8 hours. The reaction mixture was then allowed to continue stirring overnight. NMR analysis showed the reaction was complete. The reaction mixture was concentrated on a rotary evaporator at reduced pressure and 70° C. to remove the solvent and the excess iodomethane. The obtained product, dark tan solids, was purified by boiling in isopropyl alcohol (100 mL) to give brownish liquid and light tan solids. The mixture was left to cool down to room temperature and then diethyl ether (200 mL) was added to crystallize any dissolved product. The mixture was filtered and the solids were dried on a rotary evaporator at 26 torr and 75° C. The reaction afforded 1,1'-(1,4-cyclohexylenedimethylene)bis[1-ethylpiperidinium iodide] (49.3 g, 92.8% yield) as a light yellow solid.

The resulting diiodide salt was exchanged to the corresponding dihydroxide derivative by stirring it with OH-ion exchange resin (185 g, BIO-RAD® AH1-X8) in deionized water (150 mL) overnight. The solution was filtered and the filtrate was analyzed for hydroxide concentration by titration on a small sample. The exchange afforded the desired 1,1'-(1,4-cyclohexylenedimethylene)bis[1-ethylpiperidinium hydroxide] in 98% yield as a 0.65 molar solution.

Example 3

Synthesis of 1,1'-(1,4-cyclohexylenedimethylene)bis [1-methylpyrrolidinium hydroxide]

The 1,1'-(1,4-cyclohexylenedimethylene)bis[1-methylpyrrolidinium hydroxide] was prepared in a similar fashion to the procedure described in Example 1 with the exception of using pyrrolidine in place of piperidine. The resulting aqueous 1,1'-(1,4-cyclohexylenedimethylene)bis[1-methylpyrrolidinium hydroxide] solution had a concentration of 0.63 M.

Example 4

Synthesis of 1,1'-(1,4-cyclohexylenedimethylene)bis [1-ethylpyrrolidinium hydroxide]

The 1,1'-(1,4-cyclohexylenedimethylene)bis[1-ethylpyrrolidinium hydroxide] was prepared in a similar fashion to the procedure described in Example 2 with the exception of using pyrrolidine in place of piperidine.

Example 5

Synthesis of aluminosilicate SSZ-16 (Al-SSZ-16) with 1,1'-(1,4-cyclohexylenedimethylene)bis[1-methylpiperidinium hydroxide]

In a 23 mL Teflon liner, 3.1 g of a 0.65M solution of 1,1'-(1,4-cyclohexylenedimethylene)bis[1-methylpiperidinium hydroxide] solution, 0.2 g of a 1N aqueous NaOH solution, 0.25 g of Na—Y zeolite, 2.5 g of sodium silicate solution, and 3 g of deionized water were mixed thoroughly until a homogenous mixture was obtained. The Teflon liner was capped and sealed in a Parr autoclave. The autoclave was affixed on a rotating spit (43 rpm) in a heated oven at 150° C. The autoclave was heated for 6 days. Scanning Electron Microscopy indicated reaction completion by full crystallinity of the products. The reaction mixture (with a clear liquid layer and settled fine powdery material and a pH of >12.0-12.8) was filtered. The obtained fine solids were thoroughly rinsed with water. The products were left to dry in open air overnight and then dried in a heated oven at 125° C. for 1 hour. The reaction afforded 0.53 g of pure crystalline SSZ-16 zeolite as indicated SEM and powder XRD analysis.

Figure 1:
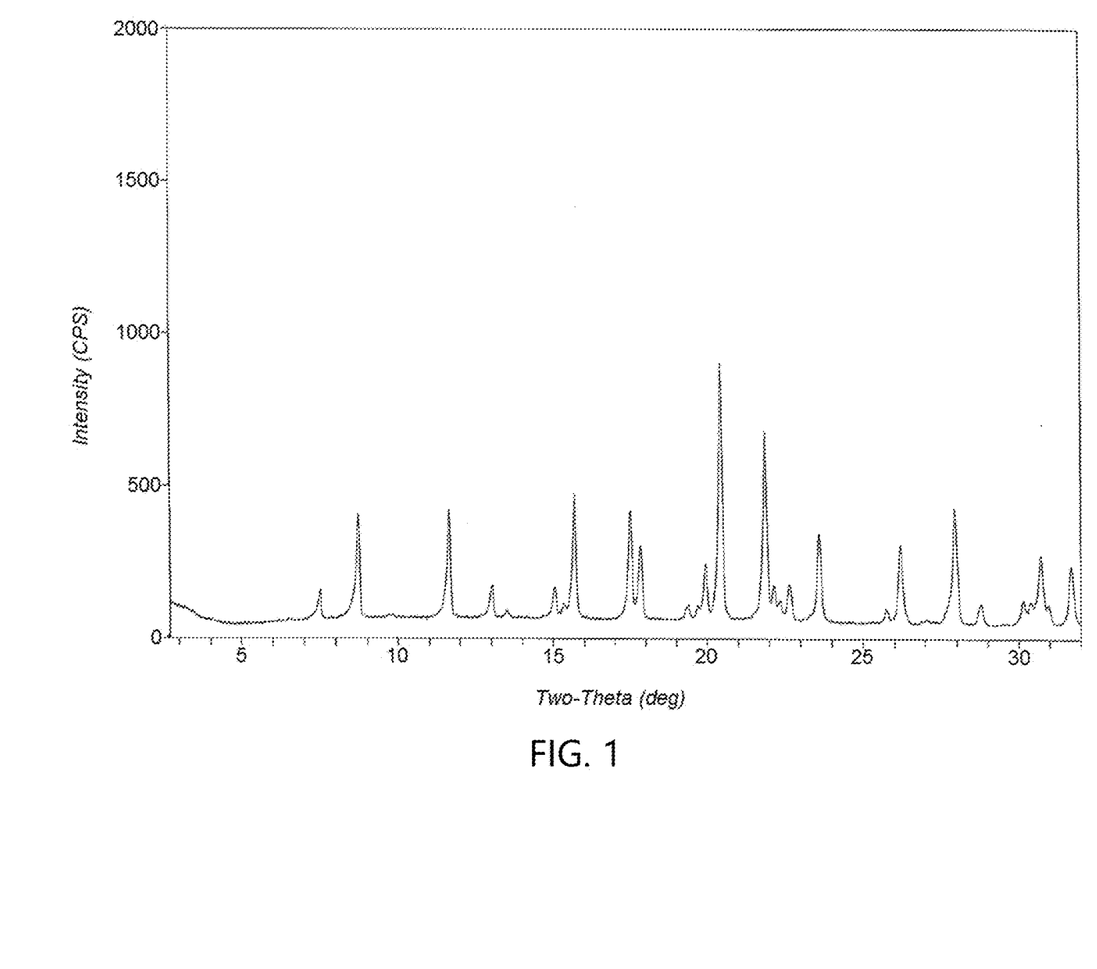
FIG. 1 is a powder X-ray diffraction (XRD) pattern of the as-synthesized zeolite prepared in Example 5.
Figure 2:
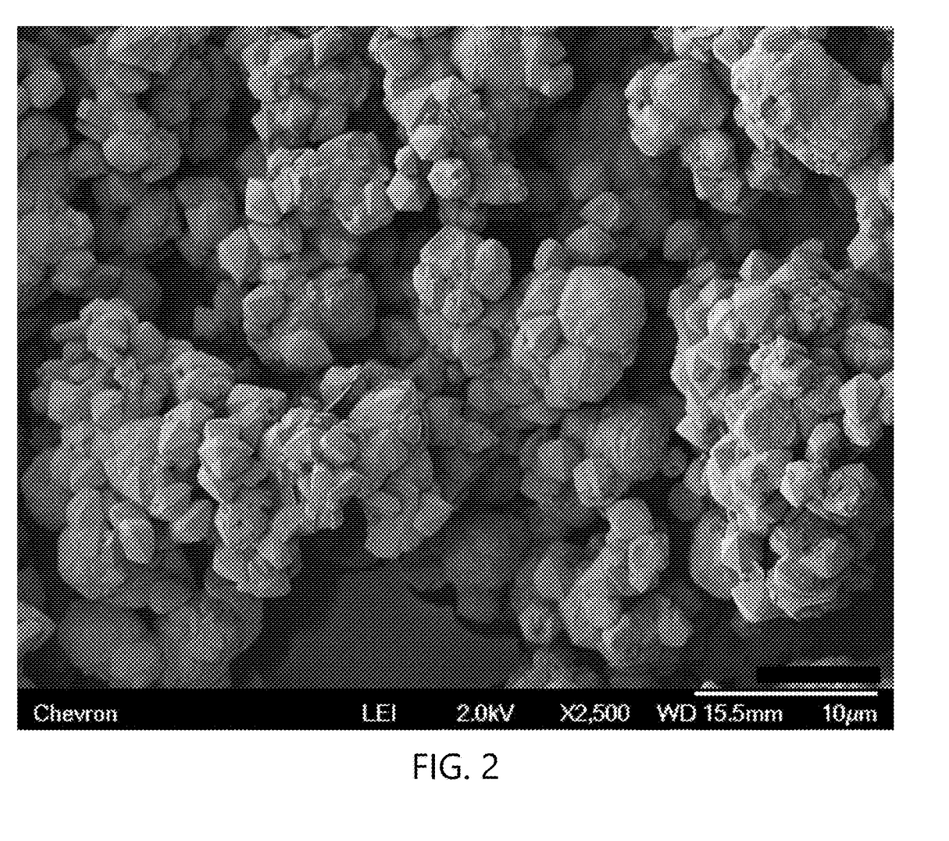
FIG. 2 is a Scanning Electron Micrograph (SEM) image of the as-synthesized zeolite prepared in Example 5.

The powder XRD pattern and SEM image of the resulting as-synthesized zeolite product are shown in FIG. 1 and FIG. 2, respectively. The lines of the X-ray diffraction pattern of the as-synthesized zeolite product are given in Table 4.

TABLE 4

| 2-Theta | d-spacing (nm) | Relative Intensity[a] |
|---|---|---|
| 6.16 | 1.434 | M |
| 7.32 | 1.207 | M |
| 8.34 | 1.059 | M |
| 16.71 | 0.530 | W |
| 17.20 | 0.515 | W |
| 18.24 | 0.486 | W |
| 18.52 | 0.479 | W |
| 20.88 | 0.425 | VS |
| 21.40 | 0.415 | W |
| 22.12 | 0.402 | W |
| 22.56 | 0.394 | S |
| 24.81 | 0.359 | W |
| 25.44 | 0.350 | M |
| 27.27 | 0.327 | W |
| 27.66 | 0.322 | W |
| 29.64 | 0.301 | W |
| 35.80 | 0.251 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

Example 6

Calcination of Al-SSZ-16

The as-synthesized product from Example 5 was calcined in air in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. at held at 595° C. for 5 hours. There was a weight loss of 17% which is typical for the loss of the structure directing agent from cavities and pores of SSZ-16.

Figure 3:
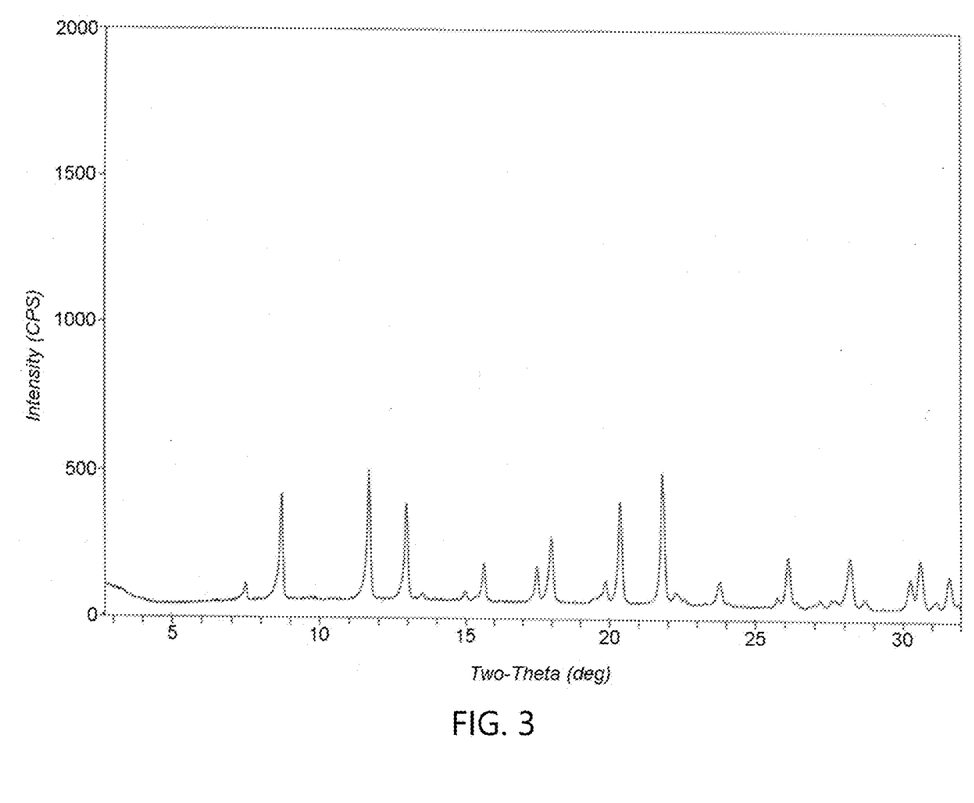
FIG. 3 is a powder XRD pattern of the calcined zeolite prepared in Example 6.

The powder XRD pattern of the calcined zeolite is shown in FIG. 3 and indicates that the material remains stable after removal of the structure directing agent. The lines of the X-ray diffraction pattern of the calcined zeolite product are given in Table 5.

TABLE 5

| 2-Theta | d-spacing (nm) | Relative Intensity[a] |
|---|---|---|
| 7.49 | 1.180 | W |
| 8.73 | 1.012 | VS |
| 11.69 | 0.756 | VS |
| 12.98 | 0.682 | VS |
| 14.96 | 0.592 | W |
| 15.65 | 0.566 | M |
| 17.50 | 0.507 | M |
| 18.00 | 0.493 | S |
| 19.88 | 0.446 | M |
| 20.38 | 0.435 | VS |
| 21.84 | 0.407 | VS |
| 22.32 | 0.398 | W |
| 23.79 | 0.374 | M |
| 25.75 | 0.346 | W |
| 26.13 | 0.341 | M |
| 26.38 | 0.338 | W |
| 27.56 | 0.323 | M |
| 28.19 | 0.316 | S |
| 30.24 | 0.295 | M |
| 30.57 | 0.292 | S |
| 31.16 | 0.287 | W |
| 31.91 | 0.280 | W |
| 33.87 | 0.264 | M |
| 34.27 | 0.261 | W |
| 34.76 | 0.258 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

Example 7

Example 5 was repeated except that 3.4 g of the structure directing agent was used and no NaOH was added. The reaction afforded 0.54 g of SSZ-16 after 6 days of heating.

Example 8

Synthesis of Al-SSZ-16 with 1,1'-(1,4-cyclohexylenedimethylene)bis[1-ethylpiperidinium hydroxide]

Example 4 was repeated but the SDA was replaced with 3.2 g of a 0.65M solution of 1,1'-(1,4-cyclohexylenedimethylene)bis[1-ethylpiperidinium hydroxide]. After 6 days of heating, the synthesis afforded 0.55 g of SSZ-16 (0.55 g) with a trace amount of mordenite (MOR) impurity.

Example 9

Synthesis of Al-SSZ-16 with colloidal aluminosilicate and 1,1'-(1,4-cyclohexylenedimethylene)bis[1-methylpiperidinium hydroxide]

In a 23 mL Teflon liner, 3.1 g of a 0.65M solution of 1,1'-(1,4-cyclohexylenedimethylene)bis[1-methylpiperidinium hydroxide], 3 g of a 1N aqueous KOH solution, and 5.25 g of a colloidal aluminosilicate (TX-15595, provided by Nalco Company) were mixed thoroughly until a homogenous mixture was obtained. The Teflon liner was capped and sealed in a Parr autoclave. The autoclave was affixed on a rotating spit (43 rpm) in a heated oven at 170° C. The autoclave was heated for 12 days. SEM indicated reaction completion by full crystallinity of the products. The reaction mixture, a paste at a pH of 11.8, was filtered. The obtained fine solids were thoroughly rinsed with deionized water. The products were left to dry in open air followed by drying an oven at 125° C. for 1 hour. The reaction afforded 4.6 g of pure crystalline SSZ-16 zeolite as indicated by SEM and powder XRD analysis.

Example 10

Synthesis of Al-SSZ-16 with 1,1'-(1,4-cyclohexylenedimethylene)bis[1-methylpyrrolidinium hydroxide]

In 23 mL Teflon liner, 3.2 g of 0.63M solution of a 1,1'-(1,4-cyclohexylenedimethylene)bis[1-methylpyrrolidinium hydroxide], 0.2 g of a 1N aqueous NaOH solution, 0.25 g of Na—Y zeolite, 2.5 g of sodium silicate solution, and 2.9 g of deionized water were mixed thoroughly until a homogenous mixture was obtained. The Teflon liner was capped and sealed in a Parr autoclave. The autoclave was affixed on a rotating spit (43 rpm) in a heated oven at 150° C. The autoclave was heated for 6 days. Scanning Electron Microscopy indicated reaction completion by full crystallinity of the products. The reaction mixture (with a clear liquid layer and settled fine powdery material and a pH of >12.2-12.8) was filtered. The obtained fine solids were thoroughly rinsed with water. The products were left to dry in open air overnight and then was dried in a heated oven at 125° C. for 1 hour. The reaction afforded 0.46 g of SSZ-16 and MOR (in about 40:60 ratio) as determined by SEM and powder XRD analysis.

Example 11

Synthesis of Al-SSZ-16 with colloidal aluminosilicate and 1,1'-(1,4-cyclohexylenedimethylene)bis[1-methylpyrrolidinium hydroxide]

In a 23 mL Teflon liner, 3.2 g of a 0.63M solution of 1,1'-(1,4-cyclohexylenedimethylene)bis[1-methylpyrrolidinium hydroxide], 3 g of a 1N aqueous KOH solution, and 5.25 g of a colloidal aluminosilicate (TX-15595, provided by Nalco Company) were mixed thoroughly until a homogenous mixture was obtained. The Teflon liner was capped and sealed in a Parr autoclave. The autoclave was affixed on a rotating spit (43 rpm) in a heated oven at 170° C. The autoclave was heated for 12 days. SEM indicated reaction completion by full crystallinity of the products. The reaction mixture, a paste at a pH of 11.8, was filtered. The obtained fine solids were thoroughly rinsed with deionized water. The products were left to dry in open air followed by drying an oven at 125° C. for 1 hour.

The reaction afforded 0.5 g of SSZ-16 molecular sieve with a trace of amount of mordenite (MOR) as indicated by SEM and powder XRD analysis.

Example 12

Synthesis of Al-SSZ-16 with colloidal aluminosilicate and 1,1'-(1,4-cyclohexylenedimethylene)bis[1-ethylpyrrolidinium hydroxide]

Example 10 was repeated except that 1,1'-(1,4-cyclohexylenedimethylene)bis[1-ethylpyrrolidinium hydroxide] was used as a structure directing agent.

Powder XRD showed the product to be a mixture of SSZ-16 and mordenite.

Example 13

Synthesis of Al-SSZ-16 with 1,1'-(1,4-cyclohexylenedimethylene)bis[1-ethylpiperidinium hydroxide]

A 23 mL Teflon liner was charged with 1.73 g of sodium silicate solution, 0.13 g of a 1N NaOH solution, 0.18 g of CBV300 Y-zeolite (Zeolyst International; $SiO_2/Al_2O_3$ molar ratio=5.1), 2.14 g of a 1,1'-(1,4-cyclohexylenedimethylene)bis[1-ethylpiperidinium hydroxide] solution, and 1.33 g of deionized water. The composition of the reaction mixture, in terms of molar ratios, is reported in Table 6.

TABLE 6

| | |
|---|---|
| $SiO_2/Al_2O_3$ | 32.2 |
| $Na/SiO_2$ | 0.52 |
| $Q/SiO_2$ | 0.14 |
| $H_2O/SiO_2$ | 24.7 |

The Teflon liner was then capped and sealed within a steel Parr autoclave. The autoclave was placed on a spit within a convection oven at 135° C. The autoclave was tumbled at 43 rpm for 5 days in the heated oven. The autoclave was then removed and allowed to cool to room temperature. The solids were then recovered by filtration and washed thoroughly with deionized water. The solids were allowed to dry at room temperature.

The resulting zeolite product was identified by powder XRD as SSZ-16.

The product had a $SiO_2/Al_2O_3$ molar ratio of 12.5, as determined by ICP elemental analysis.

Example 14

Synthesis of Al-SSZ-16 with 1,1'-(1,4-cyclohexylenedimethylene)bis[1-ethylpiperidinium hydroxide]

A 23 mL Teflon liner was charged with 1.64 g of a sodium silicate solution, 1.06 g of a 1N NaOH solution, 0.22 g of CBV300 Y-zeolite (Zeolyst International; $SiO_2/Al_2O_3$ molar ratio=5), 1.84 g of a 1,1'-(1,4-cyclohexylenedimethylene)bis[1-ethylpiperidinium hydroxide] solution, and 3.12 g of deionized water. The composition of the reaction mixture, in terms of molar ratios, is reported in Table 7.

TABLE 7

| | |
|---|---|
| $SiO_2/Al_2O_3$ | 25.4 |
| $Na/SiO_2$ | 0.59 |
| $Q/SiO_2$ | 0.12 |
| $H_2O/SiO_2$ | 37.9 |

The Teflon liner was then capped and sealed within a steel Parr autoclave. The autoclave was placed on a spit within a convection oven at 135° C. The autoclave was tumbled at 43 rpm for 5 days in the heated oven. The autoclave was then removed and allowed to cool to room temperature. The solids were then recovered by filtration and washed thoroughly with deionized water. The solids were allowed to dry at room temperature.

The resulting zeolite product was identified by powder XRD as SSZ-16.

Example 15

Synthesis of Al-SSZ-16 with 1,1'-(1,4-cyclohexylenedimethylene)bis[1-ethylpiperidinium hydroxide]

A 23 mL Teflon liner was charged with 1.56 g of a sodium silicate solution, 0.83 g of a 1N NaOH solution, 0.27 g of CBV300 Y-zeolite (Zeolyst International; $SiO_2/Al_2O_3$ molar ratio=5.1), 1.64 g of a 1,1'-(1,4-cyclohexylenedimethylene) bis[1-ethylpiperidinium hydroxide] solution, and 0.16 g of deionized water. The composition of the reaction mixture, in terms of molar ratios, is reported in Table 8.

TABLE 8

| | |
|---|---|
| $SiO_2/Al_2O_3$ | 21 |
| $Na/SiO_2$ | 0.54 |
| $Q/SiO_2$ | 0.11 |
| $H_2O/SiO_2$ | 19 |

The Teflon liner was then capped and sealed within a steel Parr autoclave. The autoclave was placed on a spit within a convection oven at 135° C. The autoclave was tumbled at 43 rpm for 5 days in the heated oven. The autoclave was then removed and allowed to cool to room temperature. The solids were then recovered by filtration and washed thoroughly with deionized water. The solids were allowed to dry at room temperature.

The resulting zeolite product was identified by powder XRD as SSZ-16.

The product had a $SiO_2/Al_2O_3$ molar ratio of 10.5, as determined by ICP elemental analysis.

Example 16

Seeded Synthesis of Al-SSZ-16

Example 13 was repeated except that SSZ-16 seed crystals (18 mg) from a previous synthesis were added to the reaction mixture. The resulting zeolite product was identified by powder XRD as SSZ-16.

Example 17

Seeded Synthesis of Al-SSZ-16

Example 14 was repeated except that SSZ-16 seed crystals (18 mg) from a previous synthesis were added to the reaction mixture. The resulting zeolite product was identified by powder XRD as SSZ-16.

Example 18

Seeded Synthesis of Al-SSZ-16

Example 15 was repeated except that SSZ-16 seed crystals (18 mg) from a previous synthesis were added to the reaction mixture. The resulting zeolite product was identified by powder XRD as SSZ-16.

The invention claimed is:

1. An organic nitrogen-containing compound having one of the following structures:

* * * * *